May 27, 1975
J. C. MIKKELSEN
Plant Pat. 3,723
BEGONIA PLANT
Filed Feb. 28, 1974
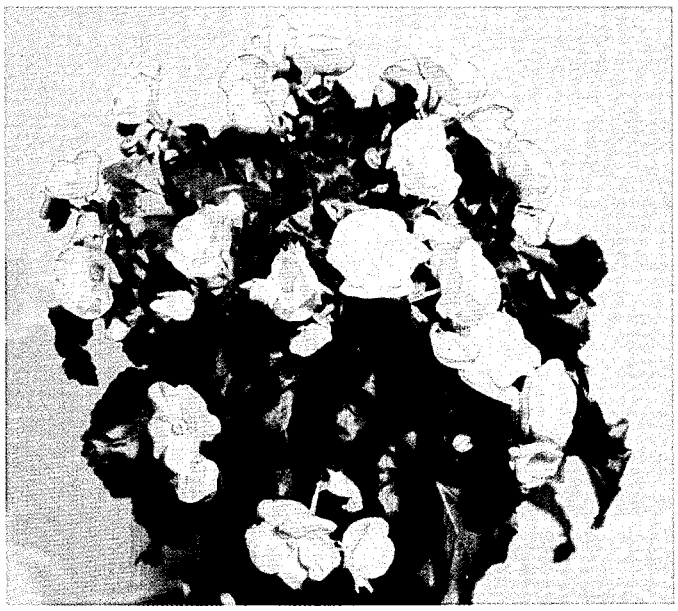

United States Patent

Plant Pat. 3,723

Patented May 27, 1975

1

3,723

BEGONIA PLANT

James C. Mikkelsen, Ashtabula, Ohio, assignor to Mikkelsens Inc., Ashtabula, Ohio Filed Feb. 28, 1974, Ser. No. 446,784

Int. Cl. A01h 5/00

U.S. Cl. Plt—68 1 Claim

The present invention relates to a new and distinctive cultivar of begonia plant, known by the varietal name Improved Schwabenland Orange and botanically known as *Begonia elatior*. The new cultivar was discovered by me as a flowering mutation in a crop of the parent cultivar Krefeld Orange, disclosed in U.S. Plant Pat. 3,403, granted Sept. 18, 1973, to Siegfried Merholz. The mutation was discovered arising from the base of a petiole of a leaf cutting all other shoots of which were of the parent Krefeld Orange. Asexual reproduction by leaf cuttings at the greenhouses of Mikkelsens Inc., Ashtabula, Ohio, has reproduced the unique features of the new variety through successive propagations.

The following characteristics distinguish the new begonia from both its parent and other begonias commercially known and used in the floriculture industry:

1. The new variety has dark spinach green leaves compared to the red pigmented leaves of the parent Krefeld Orange.
2. Growth is more vigorous than parent.
3. In propagation by leaf cuttings, a greater quantity of adventitious buds are produced on the base of leaf petiole in a shorter period of time than on parent.
4. Flower color is a sharper, more distinct shade of orange than the parent and the unpatented but commercial cultivar Schwabenland Orange.
5. The natural placement of flowers on the plant is more distinctive than on other orange flowering plants of this type.
6. Keeping qualities in the home are excellent.
7. Flowering is 7–10 days faster than on the parent Krefeld Orange, averaging 9–10 weeks in high light periods and approximately 14 weeks in low light periods.
8. Can be flowered year around by proper manipulation of environment.

The accompanying colored photographic drawing illustrates the overall appearance of this variety taken as a face view of the plant and showing the colors as true as it is reasonably possible to obtain in a colored reproduction of this type.

The following is a detailed description of my new begonia variety based on plants produced under commercial practices in the greenhouses of Mikkelsens Inc., Ashtabula, Ohio. Color references are made to the Royal Horticultural Society Colour chart except where general color terms of ordinary dictionary significance are used.

Parentage: Mutation from Krefeld Orange, disclosed in U.S. Plant Pat. No. 3,403.

Propagation: By leaf cuttings that very readily root and produce a higher quantity of adventitious shoots than other begonias in this class.

Rooting habit: Quite fibrous roots are produced within 25–30 days at 21°–23° C. bottom temperature.

2

Form: Quite fine and fibrous.

Habit of growth: Generally upright, compact, with good vigor for self support. When fully grown, the new cultivar is approximately 12″–14″ in height and 10″–12″ in diameter.

Blooming habits: Profuse flowering, with individual flowers being carried on cymes with shorter sturdier stems than the other orange type Rieger begonias.

Blooming season: Natural season in northern areas is late November. Since it can be propagated by leaf cuttings and manipulated with temperature and daylength, the new variety can be flowered any time of the year.

Foliage: Alternate, borne at slight angle to stem.

*Size.*—Varying as to the position on the plant and the environment. Leaves when mature are approximately 10–12 cm. in diameter.

*Shape.*—Cordate, crenate, veins recessed on upper surface.

*Texture.*—Upper side glabrous.

*Margin.*—Slightly indented and wavy.

*Color.*—Old top—Slightly darker than 147A. Under—138A–B. New top—137B. Under—148B.

Disease resistance: Excellent against powdery mildew. Present indications are that resistance to botrytis is somewhat less than other varieties grown under same environmental conditions.

Flowers:

*Borne.*—On cymes with heavy stems originating at the upper leaf axis. Individual cymes will continue to initiate flowers for longe periods of time; under proper conditions up to 6–8 months. Individual blooms last approximately 2–4 weeks.

*Quantity*—Very profuse.

*Buds.*—Initially flat, developing into nearly symmetrical flowers at maturity.

*Tepals.*—Normally four in number, flat with orange/red color between 33A–32A, as compared with orange-red color (40A) of Krefeld Orange and color of Schwabenland Orange (30A).

Reproductive organs:

*Stamens.*—Quite abundant, color yellow 10A when immature to 23A when mature.

*Pollen.*—Yellow 10A.

*Styles/ovaries.*—None observed to date.

I claim:

1. A new and distinct cultivar of *elatior* begonia characterized particularly by its sharper, more distinct orange flower color; dark spinach green leaves; vigorous growth habit; in propagation by leaf cuttings, a greater quantity of adventitious buds are produced on the base of the leaf petiole in a shorter period of time than on parent cultivar Krefeld Orange; distinctive natural placement of flowers on plant; excellent keeping qualities; 7–10 days faster flowering than parent, and by its year around flowering under controlled environment.

No references cited.

ROBERT E. BAGWILL, Primary Examiner